US00PP34814P2

(12) United States Plant Patent
Rullo

(10) Patent No.: US PP34,814 P2
(45) Date of Patent: Dec. 13, 2022

(54) SWEET CHERRY TREE NAMED 'JT1'

(50) Latin Name: *Prunus avium*
Varietal Denomination: JT1

(71) Applicant: Fivefifty5 Super Foods Pty Ltd, Shepparton East (AU)

(72) Inventor: Joseph Rullo, Shepparton East (AU)

(73) Assignee: Fivefifty5 Super Foods Pty Ltd, Shepparton East (AU)

( * ) Notice: Subject to any disclaimer, the term of this patent is extended or adjusted under 35 U.S.C. 154(b) by 0 days.

(21) Appl. No.: 17/662,183

(22) Filed: May 5, 2022

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181
CPC ... A01H 5/08; A01H 5/00; A01H 5/02; A01H 6/74; A01H 6/7445; A01H 6/7427
See application file for complete search history.

(56) References Cited

U.S. PATENT DOCUMENTS

PP29,317 P3 * 5/2018 Maillard ..... A01H 6/7445 Plt./181

OTHER PUBLICATIONS

Plant Varieties Journal, IP Australia vol. 33, No. 3, 2020, pp. 1 and 11. (Year: 2020).*

* cited by examiner

*Primary Examiner* — June Hwu
(74) *Attorney, Agent, or Firm* — Michelle Bos Legal LLC

(57) ABSTRACT

A sweet cherry tree named 'JT1' distinguished by its crisp, heart-shaped fruit and early season harvest maturity.

7 Drawing Sheets

Latin name: *Prunus avium.*
Variety denomination: 'JT1'.

BACKGROUND AND SUMMARY OF THE VARIETY

The new sweet cherry tree named 'JT1' originated as a seedling obtained from the open pollination of an 'Earlise' sweet cherry tree (not patented) in an established cherry orchard at Shepparton, Victoria, Australia. The seedling was first observed in 2014 when fruiting, and was first asexually propagated by bud-stick grafting onto 'Mazzard' cherry rootstock (not patented) at Shepparton, Victoria, Australia in 2016. The 'JT1' sweet cherry tree was initially selected for its crisp, heart-shaped fruit and early season fruit maturity. A comparison of the characteristics of the 'JT1' sweet cherry variety to female parent variety 'Earlise' is shown in Table 1.

TABLE 1

Comparison of 'JT1' to parent variety 'Earlise'

| Characteristic | 'JT1' | 'Earlise' |
|---|---|---|
| Fruit shape | Cordate | Reniform |
| Fruit skin color | Red | Dark red |
| Fruit firmness | Medium to high | Medium |
| Fruit sweetness | High | Low |
| Flower bloom time | Early | Medium |

The 'JT1' sweet cherry tree is distinguished from similar variety 'Royal Tioga' (U.S. Plant Pat. No. 22,779) as set forth in Table 2.

TABLE 2

Comparison of 'JT1' to similar variety 'Royal Tioga'

| Characteristic | 'JT1' | 'Royal Tioga' |
|---|---|---|
| Fruit shape | Cordate | Globose |
| Fruit skin color | Red | Red |
| Fruit firmness | Medium to high | Very high |
| Fruit sweetness | High | Medium to high |
| Flower bloom time | Early | Early |
| Pollination Requirement | Pollinator required | Self-fertile |

The 'JT1' sweet cherry tree has been found to retain its distinctive characteristics through successive asexually propagated generations.

BRIEF DESCRIPTION OF THE PHOTOGRAPHS

The accompanying photographs were obtained in 2021 at Shepparton, Victoria, Australia. The trees shown were planted in 2016.

Figure 1:
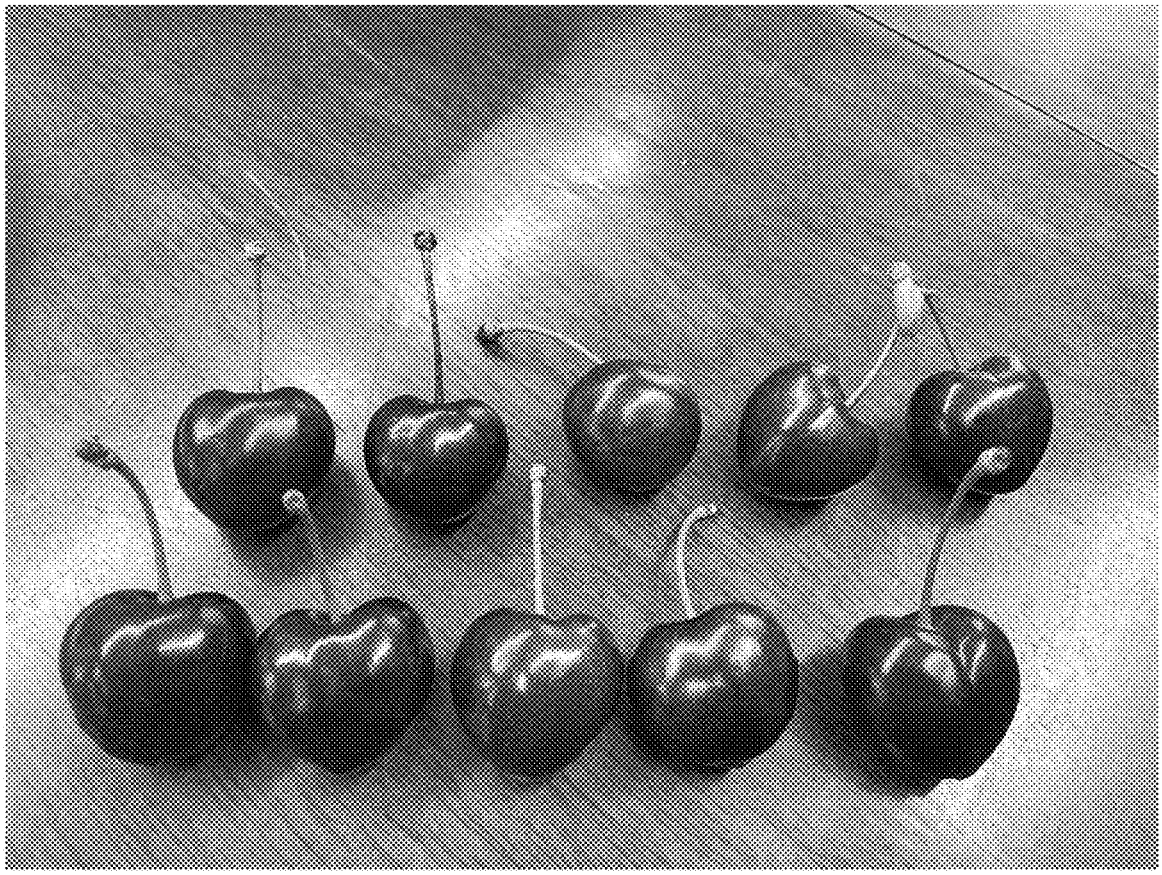
FIG. 1 shows fruit from a 'JT1' sweet cherry tree.

The colors shown in these photographs may vary with lighting conditions. Color characteristics of the claimed plant should therefore be determined with reference to the observations described herein, rather than from the photographs alone.

DETAILED BOTANICAL DESCRIPTION

The following detailed botanical description is based on observations of 'JT1' trees growing on 'Mazzard' cherry rootstock (not patented). The described trees were planted in 2016 at Shepparton, Victoria, Australia. Observations were recorded during the 2021 growing season. The characteristics described will vary somewhat depending upon cultural practices and climatic conditions, and will vary with location and season. Quantified measurements are expressed as an average of measurements taken from a number of individual plants of the new variety. The measurements of any individual plant, or any group of plants, of the new variety may vary from the stated average. Color descriptions are made with reference to The R.H.S. Colour Chart (Royal Horticultural Society 1995).

Tree:
- *Height*.—Approximately 2.9 m to top of flushing branches.
- *Spread*.—Approximately 2.7 m.
- *Vigor*.—Moderate to vigorous.
- *Habit, shape*.—Semi-upright spreading (grown on two dimensional palmette trellis).
- *Density*.—Moderate.
- *Productivity*.—Moderate; about 25 kg per tree.
- *Bearing*.—On spurs and whips.

Trunk:
- *Diameter*.—7.6 cm at 30 cm above graft union.
- *Color*.—Brown 200C.
- *Texture*.—Smooth to slightly rough, with no signs of cracking.
- *Lenticel shape*.—Elliptical, arranged horizontally.
- *Lenticel length*.—5 mm to 11 mm.
- *Lenticel width*.—1.7 mm to 2.7 mm.
- *Lenticel color*.—Greyed-orange 164A.
- *Lenticel density*.—2 to 3 per $cm^2$.

Branches:
- *Terminal shoot length*.—35 cm to 95 cm; average 47 cm.
- *Diameter at base of terminal shoot*.—3.7 mm to 9.3 mm; average 6.3 mm.
- *Diameter at end of terminal shoot*.—3.1 mm to 5.7 mm; average 4.0 mm.
- *Primary scaffold branch diameter at base*.—17.0 mm to 37.0 mm; average 23.5 mm.
- *Secondary scaffold branch diameter at base*.—11.0 mm to 21.0 mm; average 17.5 mm.
- *Diameter at base of fruit hanging limbs*.—5.0 mm to 13.0 mm; average 8.5 mm.
- *Diameter at base of fruiting spurs*.—6.2 mm to 9.7 mm; average 7.1 mm.
- *Texture*.—Smooth on first year wood, with increasing. longitudinal peeling of epidermis as branch ages.
- *Pubescence on branches*.—Absent or non-conspicuous.
- *Fruiting branch diameter* (2+ *year wood*).—8.5 mm to 13.2 mm; average 10.8 mm.
- *Fruiting branch color*.—Brown 200C.
- *Lenticel shape* (2+ *year wood*).—Elliptical, arranged horizontally.
- *Lenticel length* (2+ *year wood*).—2.9 mm to 4.2 mm.
- *Lenticel width* (2+ *year wood*).—1.5 mm to 2.1 mm.
- *Lenticel color* (2+ *year wood*).—Brown 200A.
- *Lenticel density* (2+ *year wood*).—2 to 4 per $cm^2$.
- *Attitude of one year old shoot*.—Semi-erect to erect.
- *Shoot color* (1 *year wood*).—Brown 200B.
- *Shoot lenticel color* (1 *year wood*).—Greyed-orange 165C.
- *New wood color*.—Yellow-green 146B.
- *Branch crotch angle*.—60° to 80° (as trained on trellis).
- *Vegetative bud burst*.—Sep. 8, 2021 at Shepparton.
- *Vegetative bud length*.—6.0 mm.
- *Vegetative bud width*.—2.5 mm.
- *Vegetative bud shape*.—Conical, slightly elongated.

Flower buds:
- *Stage described*.—Budburst.
- *Bud length*.—3.7 mm to 6.9 mm; average 5.7.
- *Bud diameter*.—2.3 to 3.9 mm; average 3.0.
- *Bud shape*.—Ovoid.
- *Position relative to shoot*.—Slightly held out.
- *Color*.—Yellow-green 144A.
- *Quantity per spur*.—5 to 13; average 8.

Flowers:
- *Date of first bloom*.—Sep. 14, 2021 at Shepparton.
- *Date of full bloom*.—Sep. 29, 2021 at Shepparton.
- *Quantity of flowers per cluster*.—2 to 4; average 3.
- *Quantity of petals per flower*.—5.
- *Flower diameter*.—22 mm to 33 mm; average 27.1 mm.
- *Flower depth*.—13.5 mm to 16.0 mm; average 15.5.
- *Petal length*.—15 mm to 21 mm; average 17.8 mm.
- *Petal width*.—11 mm to 19 mm; average 15.1 mm.
- *Petal shape*.—Obovate.
- *Petal color*.—Both surfaces greyed-white 156D.
- *Petal margin*.—Entire, sinuate.
- *Relative position of petal margins*.—Overlapping to free when fully open.
- *Petal texture*.—Both surfaces glabrous.
- *Pedicel length*.—18 mm to 44 mm; average 30.6 mm.
- *Pedicel diameter*.—1.0 mm to 1.5 mm.
- *Pedicel color*.—Yellow-green 144C.
- *Fertility*.—Pollinator required.

Stamens:
- *Quantity per flower*.—36 to 44; average 39.
- *Stamen length*.—4.5 mm to 13.0 mm; average 8.3 mm.
- *Filament diameter*.—0.3 mm.
- *Filament color*.—Greyed-white 156D.
- *Anther diameter*.—0.5 mm.
- *Anther color*.—Yellow-orange 22A.
- *Abundance of pollen*.—Moderate.

Pistil:
- *Quantity per flower*.—Usually 1.
- *Fragrance*.—Moderately fragrant.
- *Position relative to anther*.—Below.
- *Length*.—17 mm to 19 mm.
- *Stigma diameter*.—1.0 mm to 1.5 mm.
- *Stigma color*.—Yellow-green 151A.
- *Style length*.—11 mm to 14 mm.
- *Style color*.—Yellow-green 145B.
- *Ovary length*.—7.5 mm to 8.5 mm.
- *Ovary color*.—Green 143C.
- *Hypanthium diameter*.—5.5 mm to 6.5 mm.
- *Hypanthium depth*.—6.5 mm to 7.5 mm.

Sepals:
- *Quantity per flower*.—5.
- *Length*.—6.5 mm to 7.5 mm; average 7.0 mm.
- *Width*.—4.0 mm to 5.5 mm; average 4.5 mm.

*Shape*.—Broad base with triangular apex; margin entire.
*Color*.—Yellow-green 144C.

Leaves:
*Arrangement*.—Alternate.
*Attitude in relation to shoot*.—Acute.
*Length*.—135 mm.
*Width*.—60 mm.
*Form*.—Lanceolate.
*Apex*.—Acuminate with pointed angle of tip.
*Base*.—Oblique rounded.
*Margin*.—Serrate.
*Thickness*.—Medium.
*Texture*.—Glabrous.
*Pubescence*.—Absent on upper surface; sparsely present on lower surface, primarily near veins.
*Color*.—Upper surface — Green 141A.
*Color*.—Lower surface — Green 143C.
*Color*.—Veins — Yellow-green 144B.
*Petiole length*.—19.7 mm.
*Petiole diameter*.—2.1 mm.
*Petiole color*.—Greyed-purple 187B.
*Petiole pubescence*.—Sparse.
*Petiole glands*.—1 to 3 reniform glands in alternate pattern on upper petiole surface at base of leaf blade.
*Gland length*.—1.0 mm to 2.2 mm.
*Gland width*.—0.5 mm to 1.5 mm.
*Stipule quantity*.—2.
*Stipule shape*.—Spinose.
*Stipule length*.—10.0 mm to 13.5 mm.
*Stipule diameter*.—0.7 mm to 3.3 mm.
*Stipule color*.—Yellow-green 144C.

Fruit:
*Maturity*.—November 16 to November 20 at Sheppar-ton.
*Weight*.—8.0 g to 12.0 g; average 9.1 g.
*Length*.—24.7 mm to 27.4 mm; average 26.0 mm.
*Diameter at widest point*.—25.6 mm to 29.4 mm; average 27.8 mm.
*Form, viewed from apex*.—Round.
*Form, viewed from suture side*.—Slightly asymmetrical.
*Form, viewed from side perpendicular to suture*.—Slightly asymmetrical.
*Suture depth*.—Minimal, visible only at apex.
*Stalk cavity depth*.—1.7 mm to 3.4 mm; average 2.6.
*Stalk cavity diameter*.—7.2 mm to 10.8 mm; average 8.7.
*Base shape*.—Rounded, pistil abscission scar evident.
*Stem length*.—30 mm to 50 mm; average 40.5.
*Stem diameter*.—1.6 mm to 1.8 mm.
*Stem color*.—Green 141C.
*Stem adhesion to stone*.—Medium to high.

Figure 2:
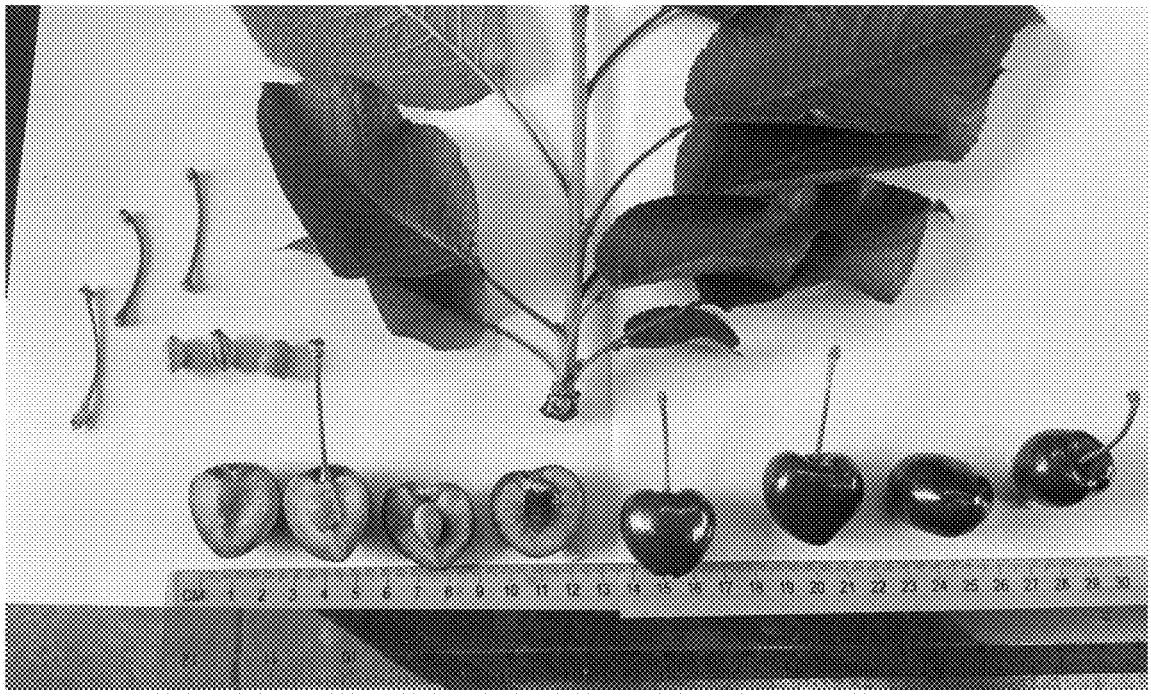
FIG. 2 shows leaves and whole and sectioned fruit from a 'JT1' sweet cherry tree.
Figure 3:
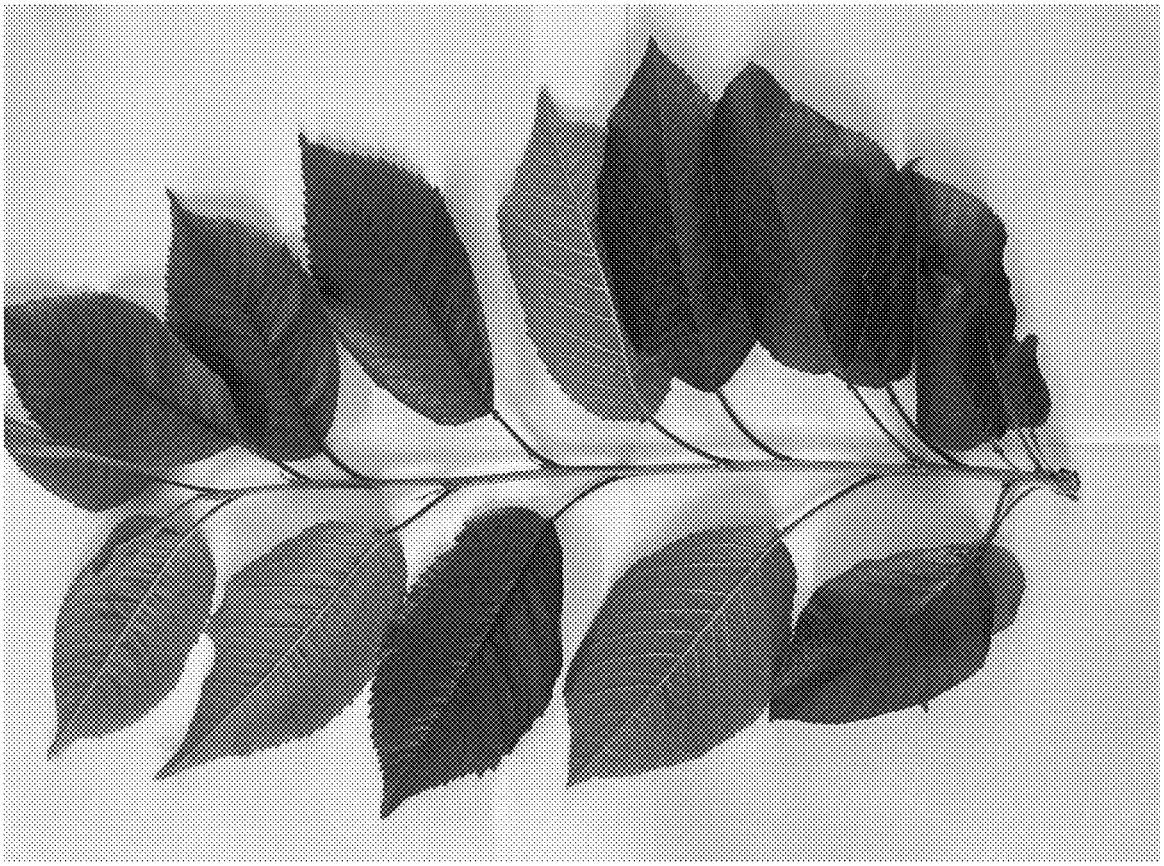
FIG. 3 shows leaves from a 'JT1' sweet cherry tree.
Figure 4:
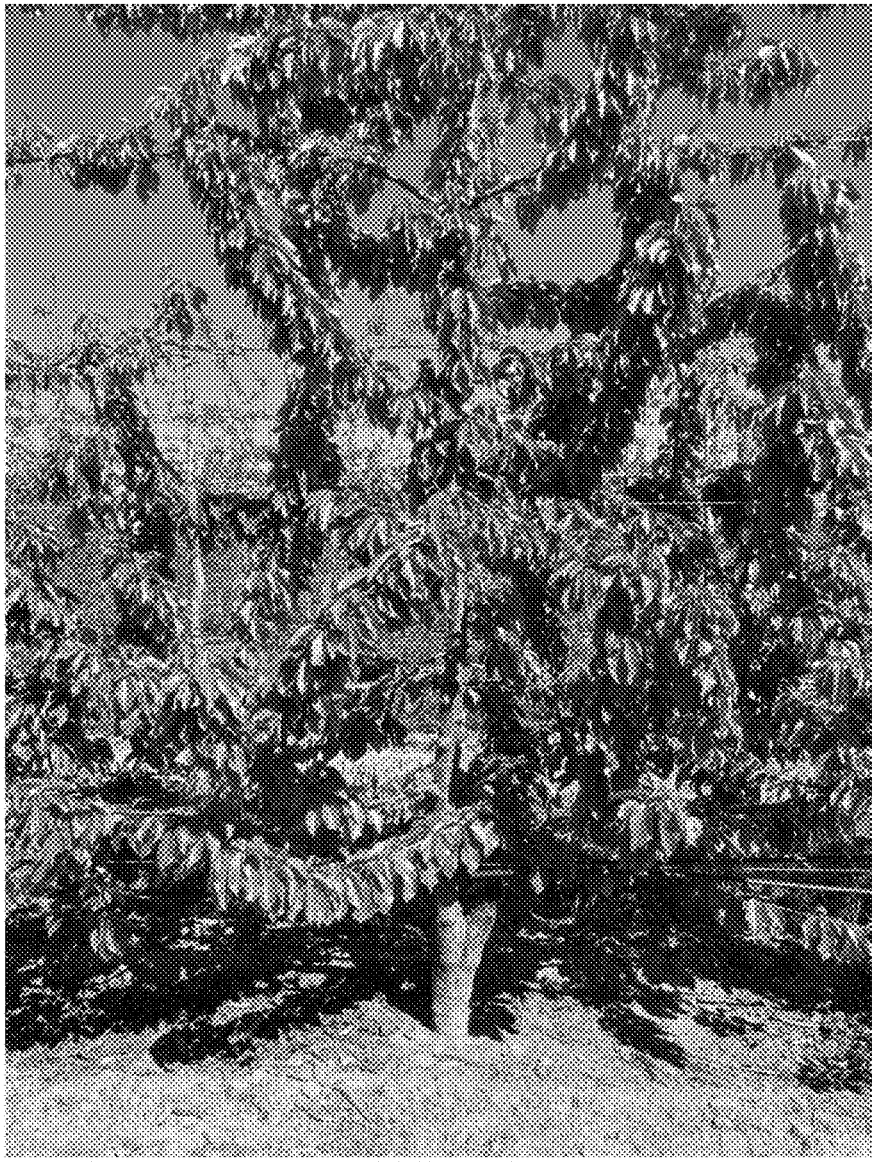
FIG. 4 shows a 'JT1' sweet cherry tree.
Figure 5:
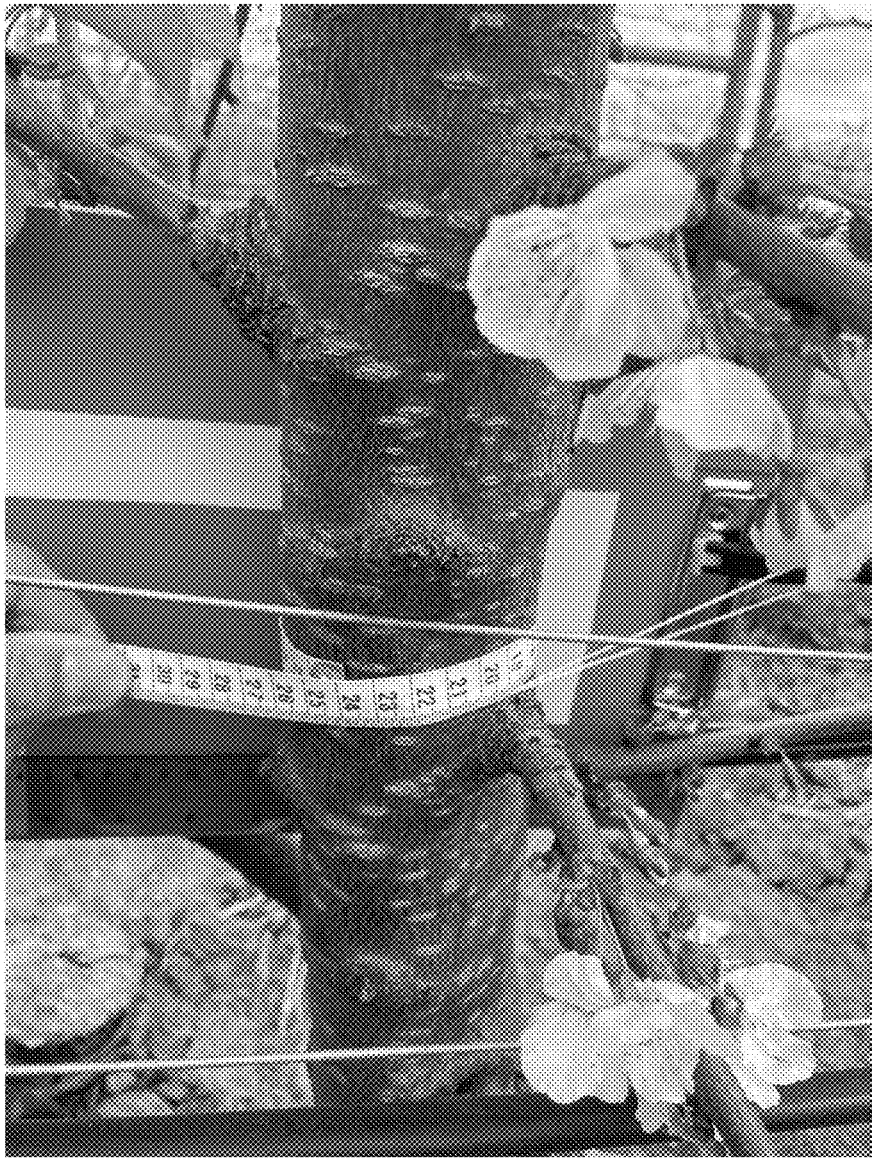
FIG. 5 shows the trunk and blossoms of a 'JT1' sweet cherry tree.
Figure 6:
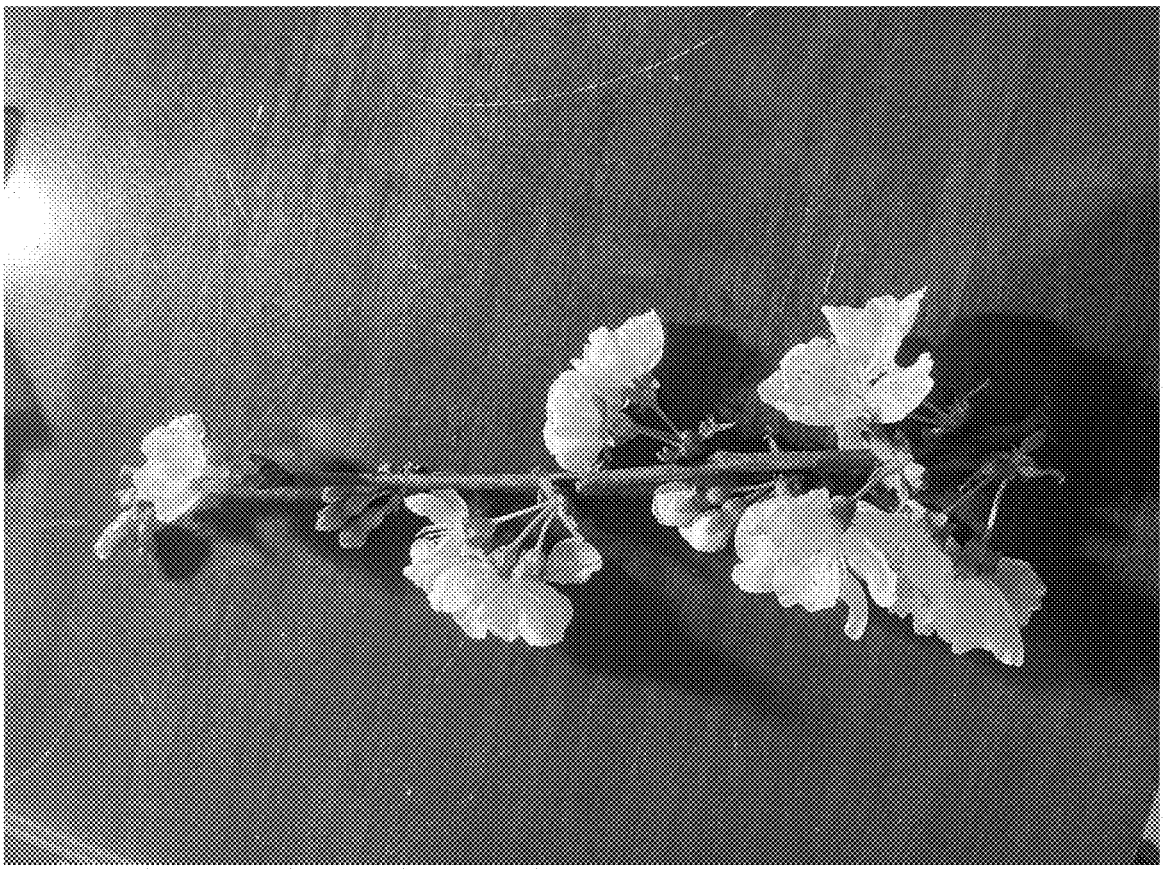
FIG. 6 shows blossoms on a branch from a 'JT1' sweet cherry tree.
Figure 7:
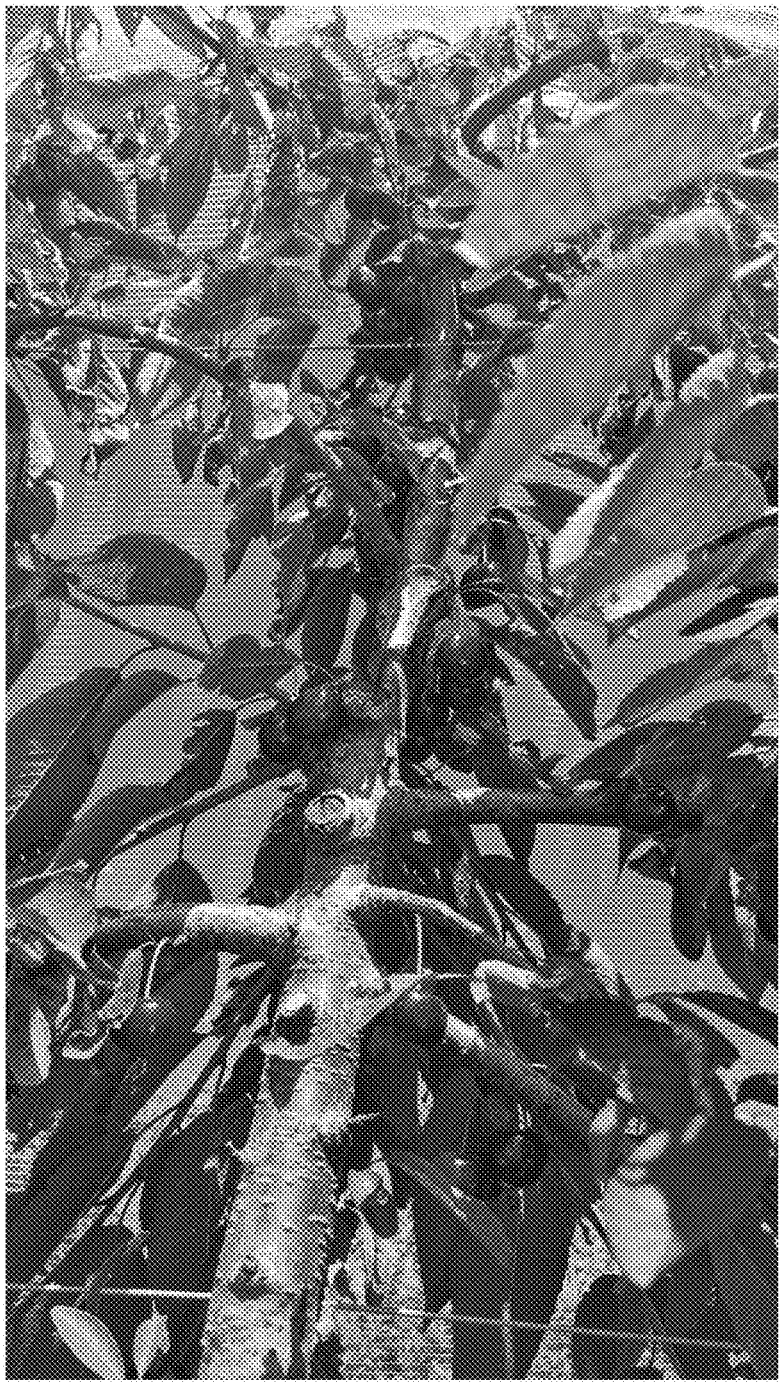
FIG. 7 shows the trunk, branches, leaves and fruit on a 'JT1' sweet cherry tree.

Fruit flesh:
*Firmness*.—Firm; 0.13 kgf to 0.45 kgf; average 0.24 kgf.
*Texture*.—Dense.
*Fibers*.—Few; fine and tender.
*Flavor*.—Very good; balanced between acid and sugar.
*Juiciness*.—Approximately 40% juice content.
*Brix*.—11.8% to 15.9%; average 14.0%.
*Flesh to stone ratio*.—9:1.
*Aroma*.—Modest.
*Flesh color*.—Greyed-yellow 160B with red-purple 59A (see FIG. 2).
*Juice color*.—Red-purple 59A.

Fruit skin:
*Thickness*.—Thin; approximately 0.165 mm.
*Texture*.—Smooth, glabrous and shiny upon brushing.
*Bloom wax*.—Inconspicuous.
*Ground color*.—Red-purple 73B.
*Overall color*.—Red 46A.
*Lenticel quantity*.—More than 170 per $cm^2$.
*Lenticel color*.—White.

Stone:
*Type*.—Semi-clingstone.
*Length*.—11.1 mm to 13.8 mm; average 12.5 mm.
*Width*.—8.1 mm to 10.5 mm; average 9.4 mm.
*Shape*.—Rounded, symmetrical.
*Surface texture*.—Slightly rough.
*Ridges*.—Broad and flat, converging at base and apex.
*Color*.—Greyed-orange 163C.
*Tendency to split*.—None.

Plant hardiness: USDA Zone 9B.
Harvest maturity: Early.
Number of picks: Select harvest over 4 days.
Use: Fresh consumption.
Susceptibility and resistance No susceptibility or resistance to known pests or diseases has been observed to date.

The invention claimed is:

1. A new and distinct sweet cherry tree named 'JT1' substantially as illustrated and described herein.

* * * * *